United States Patent
Battiste

(12) 
(10) Patent No.: US 6,723,804 B1
(45) Date of Patent: Apr. 20, 2004

(54) MONITORING AND CONTROL OF SLURRY PROCESSES FOR POLYMERIZING OLEFINS

(75) Inventor: David R. Battiste, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 126 days.

(21) Appl. No.: 09/705,315

(22) Filed: Nov. 3, 2000

(51) Int. Cl.$^7$ .................................................. C08F 2/14
(52) U.S. Cl. .............................. 526/60; 526/59; 526/64; 526/65; 526/905
(58) Field of Search .............................. 526/59, 60, 64, 526/61, 65, 905

(56) References Cited

U.S. PATENT DOCUMENTS

| | | | | |
|---|---|---|---|---|
| 5,151,474 A | * | 9/1992 | Lange et al. | 526/60 |
| 5,652,653 A | | 7/1997 | Alsmeyer et al. | 356/301 |
| 5,678,751 A | * | 10/1997 | Buchanan et al. | 228/124.6 |
| 6,479,597 B1 | * | 11/2002 | Long et al. | 526/59 |

OTHER PUBLICATIONS

Lai, et al, Noninvasive Spectroscopic Detection of Bulk Polymerization by Stimulated Raman Scattering, Applied Spectroscopy, vol. 48, No. 8, 1994, pp. 1011–1014.*

* cited by examiner

*Primary Examiner*—Fred Teskin

(57) ABSTRACT

Processes, methods and apparatus relating to olefin polymerization include the use of Raman spectrometry to monitor the concentration of reactants, products or other chemical components. One or more polymerizaton conditions are adjusted in response to those monitored concentrations. The present processes, methods and apparatus are applicable with slurry olefin polymerization process, even though such slurry processes contain solid particles were are known to interfere with Raman spectrometry. Furthermore, the present processes, methods and apparatus are applicable where there is some degree of overlap between Raman spectral peaks. Methods of monitoring and controlling olefin polymerization processes, reactants and other components use Raman spectrometry. Apparatus for olefin polymerization reactions have polymerization equipment, at least one Raman probe located in the polymerization equipment, and Raman spectrometry equipment located outside the polymerization equipment and operatively connected to at least one Raman probe.

17 Claims, 1 Drawing Sheet

US 6,723,804 B1

MONITORING AND CONTROL OF SLURRY PROCESSES FOR POLYMERIZING OLEFINS

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

This invention relates to the use of Raman spectrometry in processes for polymerizing olefins and in methods of monitoring and controlling olefin polymerization processes, reactants and other components. More particularly, a Raman fiber optic probe may be placed in an olefin polymerization reactor, or before or after such a reactor, for Raman spectrometry analysis. The present processes and apparatus may employ low resolution Raman spectrometry and measurement of liquid phase and/or gas phase components of an olefin polymerization process. The present processes and apparatus allow for quantitatively monitoring the olefin polymerization process in situ and constitute an improvement over gas chromatographic analysis conventionally employed in monitoring olefin polymerization reactions.

BACKGROUND OF THE INVENTION

Olefin monomers, such as ethylene and propylene, can be polymerized to form polyolefins. For example, ethylene or propylene may be homopolymerized to form polyethylene and polypropylene, respectively, or they may be copolymerized together or with higher 1-olefins such as 1-butene, 1-pentene, 4-methyl-1-pentene, 1-hexene and others. Processes for manufacturing polyolefins typically employ catalyst systems comprising one or more catalytic metal compounds, typically transition metals, perhaps together with a co-catalyst and/or a support such as alumina or silica. Different types of olefin polymerization processes are available. For example, olefins may be polymerized in homogeneous processes or in heterogeneous processes.

One type of polymerization process employs a slurry as the reaction mixture. In slurry polymerization processes, solid olefin polymers such as polypropylene, polyethylene and copolymers, are formed under polymerization conditions that include a slurry as the reaction mixture. The slurry comprises the solid olefin polymer particles suspended in a liquid diluent that is inert in the polymerization reaction and in which the polymer is insoluble under polymerization conditions. Typically, slurry polymerization processes are conducted in a relatively high-pressure continuous reactor, such as a loop reactor. Such reactors may be operated at pressures of about 600 psi, for example, and at temperatures of about 60 degrees C. to about 100 degrees C. In many situations, slurry polymerization processes are relatively more commercially desirable than other polymerization processes.

In the slurry polymerization process, components such as one or more monomers, a diluent, and a catalyst system and possibly other reactants (such as, for example, comonomers or hydrogen) are introduced to the polymerization reactor to form a reaction mixture. The reaction mixture is maintained under polymerization conditions for formation of polyolefin. After a suitable period, the slurry or a portion thereof is discharged from the reactor through a product take-off line into a settling leg. The solid polyolefin settles out from the slurry, leaving a clear liquid comprising diluent and reactants such as the monomer. The clear liquid and solid polyolefin then may then re-mix as they are transferred to one or more separation chambers or flash tanks where, for example, they are flashed to a low pressure such as about 15 or 20 psi. Some slurry loop polymerization equipment includes both a high pressure flash tank and a low pressure flash tank. Further information and details of slurry polymerization processes and loop reactors, including examples of suitable reaction conditions as well as control schemes for other important variables, such as solids concentration and production rate, can be found in U.S. Pat. No. 3,998,995 and U.S. Pat. No. 3,257,363, which are incorporated herein by reference.

It is desired to monitor and control the polymerization reaction so that one may obtain polyolefins having particular properties. Obtaining particular properties in a polyolefin may be done by control of the component concentrations or ratios during the polymerization process. Small changes in components can affect the properties of the final polyolefin product. Control of the concentration of olefin monomer, and if present, comonomer and hydrogen, is required to ensure reliable finished polyolefin product properties. Other important control parameters may include the degree of polymerization, molecular weight, or size of the polymer chain. Therefore, it is desirable to monitor the olefin polymerization process by determining monomer content and, when one or more co-monomers are present, by determining co-monomer content(s). It may also be desirable to determine diluent content and product content.

Current methods of monitoring slurry polymerization processes and the components (reactants, products, and diluent) in such processes are less than optimal for several reasons. In loop polymerization processes, monomer and co-monomer content have typically been determined by gas chromatography ("GC") analysis of the flash gas, that is, the gas released at one of the flash tanks where pressure is released. For example, U.S. Pat. No. 3,257,363 discloses methods of controlling the composition of the reaction mixture in a loop polymerization reactor wherein a gas chromatographic analyzer may be used to determine the amounts of ethylene and 1-butene reactants from a polymer-free off-gas line or with a sample stream from anywhere in the reaction system.

However, monitoring of the olefin polymerization process by analysis of the flash gas is less than optimal for several reasons. One reason is the amount of time for such analysis. If an analysis takes too much time, it generally has less value for monitoring, controlling or adjusting the olefin polymerization process. Also, another concern arises when the polymerization equipment includes more than one flash chamber, such as a high pressure flash chamber and a low pressure flash chamber. In such instances, gas chromatographic analysis of flash gas takes more time and is potentially less accurate when both high pressure and low pressure flash tanks are in operation.

While the contents of the olefin polymerization reactor may be determined by removing a small sample for analytical testing in a remote laboratory, this is less favorable than monitoring in situ. It may be dangerous and difficult to remove a sample from a hot process stream, and there are risks that the sample may not be representative of the overall reactor contents or that removing the sample may alter the sample. Sampling is time-consuming, and delay may cause the sample not to be representative of the reactor contents.

A significant amount of material may be produced in the time required to remove, prepare, and analyze a sample. The analytical data obtained from the delayed sample is therefore of limited value for proactive process control. Furthermore, additional processing of the extracted sample may be required yet is undesirable.

A preferred method of monitoring the polymerization process would monitor the process as it happens, or as soon thereafter as practical. It is also preferable that an analysis method be performed in situ, as opposed to being performed on samples removed from the polymerization equipment. An in situ method would reduce the need to remove samples from the production environment, improve safety, and yield faster measurements. However, there are obstacles to providing in situ on-line chemical information in a process environment. The analytical method must be sufficiently accurate and precise under hostile physical and chemical conditions. The analytical method must be capable of remote detection and analysis.

Analyses of slurry olefin polymerization processes in situ, that is, within a slurry loop polymerization reactor or associated equipment, have been difficult if not impossible to do, since such olefin polymerization reactions are carried out at high pressures. However, spectrophotometric apparatus such as a spectrograph and a radiation source can be situated in a location remote from the polymerization reactor that is to be analyzed in situ, the sampling site being connected to the apparatus by radiation conduits comprising fiber optic cables.

Raman spectrometry can provide qualitative and quantitative information about the composition and/or molecular structure of chemical components. Raman spectrometry is based upon the vibrational energy of a compound. A sample is irradiated, preferably by a monochromatic light source, and the scattered light is examined through a spectrometer using photoelectric detection. Most of the scattered radiation has the wavelength of the source radiation, which is referred to as Rayleigh scattering. However, the scattered radiation also comprises radiation at shifted wavelengths, which is referred to as Raman scattering, which occur at different wavelengths due to molecular vibrations. The difference in wavelengths between the source radiation and radiation affected by molecular vibrations is commonly referred to as the Raman shift. Even if monochromatic light is used as the source radiation, the Raman spectrum will comprise scattered light spread across a wavelength band. The Raman shift or Raman spectrum conveys compositional and molecular information regarding the component in the sample. The Raman spectrum is extremely weak compared to the Rayleigh spectrum.

Not all substances are measurable by Raman spectrometry. There must be a change in polarizability during molecular vibration of a substance in order for that substance to be Raman active.

There are several factors that have favored the use of gas chromatography as an analytical method over Raman spectrometry with olefin polymerization processes. In general, it is recognized by those familiar with Raman spectrometry that the presence of solid particles in a solution to be analyzed will significantly reduce the Raman shift observed. In particular, slurry olefin polymerization processes include solid polyolefin particles in the slurry. Also, the reactants and products in olefin polymerization processes may have peaks in their respective Raman spectra that are relatively close together, such as when ethylene is employed as a monomer and hexene is employed as a co-monomer. For example, ethylene and hexene produce similar peaks in their Raman spectra. Ethylene exhibits a peak at 1620 cm$^{-1}$ while hexene exhibits a peak at 1640 cm$^{-1}$. As a result, it may be difficult to distinguish between ethylene and hexene, and there is likely to be some overlap in certain peaks. Thus, it would appear necessary to employ high resolution Raman spectrometry equipment to analyze the components of certain olefin polymerization processes. Furthermore, Raman spectrometry equipment, particularly high resolution Raman spectrometry equipment, is relatively expensive, which would generally discourage its use with industrial processes. Gas chromatography equipment has historically been less costly than high resolution Raman spectrometry equipment. Furthermore, gas chromatography sampling systems are well established. Also, gas chromatography equipment tends to provide information that is more readily usable, whereas Raman spectrometry equipment tends to produce information that requires additional analysis. Engineers and operators tend to prefer equipment that provides a relatively simple reading rather than a spectrum.

International Application No. PCT/AU86/00076, which is incorporated herein by reference, discloses monitoring the presence or concentration of one or more chemical components by using Raman scattering. Optical fibers are used to direct electromagnetic radiation to and from the monitored environment, so that the Raman detector may be remote from the monitored environment. It is stated that the Raman monitoring method is applicable to gases, liquids and solids, though no particular chemical components are disclosed as being monitored. It is also stated that it is necessary to examine the intensity of the scattered light at selected characteristic wavelengths. A band pass filter system is used, which has a series of narrow band pass interference filters each having a band pass between 100 cm$^{-1}$ and 400 cm$^{-1}$. Each filter is chosen to give maximum transmission of the Raman scattering of a particular component to be analyzed. This international application does not disclose the use of Raman spectrometry to monitor an olefin polymerization process, or to measure olefin monomers. The international application does not disclose a method of monitoring the presence or concentration of more than one chemical component when those components have overlapping Raman spectra or event that such monitoring is possible.

U.S. Pat. No. 5,652,653, which is incorporated herein by reference, discloses a method of on-line quantitative analysis of chemical compositions by Raman spectrometry. The method comprises simultaneously irradiating the monitored chemical composition and a reference material. The method applies predetermined calibration means to the standard Raman spectrum of the analyzed chemical composition to ascertain the chemical composition. The method is used for analyzing a polyester manufacturing process. A polyester manufacturing process generally has a liquid reaction mixture that does not include solids or a slurry. The patent discloses the construction of constitution-intensity correlation (CIC) multivariate calibration means. This is done by comparing a plurality of peaks at different wavelengths in the Raman spectra, which are preferably standard spectra, with a plurality of chemical compositions of known concentrations. The wavelengths selected for construction of a CIC depend on the spectral characteristics of the particular component whose concentration in a chemical composition is to be determined. For each component whose in situ concentration in the composition is desired to be monitored at any given time, a separate CIC calibration is prepared.

U.S. Pat. No. 4,620,284, which is incorporated herein by reference, relates to qualitative and quantitative analysis using Raman scattering for substances in gaseous, liquid and solid form to provide numbers, rather than spectra, denoting the amounts of the substances present. It is disclosed that reference spectra are used to establish a relationship between spectra region areas and concentrations of substances, and that composite reference spectra may be prepared. The patent discloses a hydrocarbon analyzer dedicated to "PNA" analysis as a particular embodiment, which determines the composition of a hydrocarbon in terms of three groups: paraffins, napthlanes, and aromatics. Among the prior art disclosed in that patent is work accomplished using the Raman effect to analyze hydrocarbons, including an article entitled "Determination of Total Olefins and Total Aromatics." Similarly, an article entitled "Low-Resolution Raman Spectroscopy," Spectroscopy 13(10) October 1998, discuss Raman spectrometric analysis of mixtures of organic liquids as well as petroleum products.

However, it is believed that Raman spectrometry has not been previously employed to monitor an olefin polymerization process.

SUMMARY OF THE INVENTION

The present processes, methods, and apparatus differ from prior processes and apparatus for monitoring chemical components with Raman spectrometry in that Raman spectrometry is applied to olefin polymerization processes. Monitoring of olefin polymerization processes by Raman spectrometry is distinguishable at least because Raman spectra of the various components may overlap, and other factors have made other analytical methods appear to be superior. For example, the presence of solid polyolefin particles in the reaction mixture of some polymerization processes would discourage the use of Raman spectrometry for analyzing such reaction mixtures.

A process for olefin polymerization in a slurry comprising solid polyolefin and a diluent is provided. The process comprises the steps of contacting in a reaction mixture under slurry polymerization conditions: (i) at least one reactant including at least one olefin monomer and optionally at least one comonomer and optionally hydrogen and (ii) a heterogeneous catalyst system comprising one or more catalytic metal compounds and one or more co-catalysts; (b) making a polyolefin; and (c) monitoring the process by using Raman spectrometry equipment to provide an output signal representative of one or more of reactants or the polyolefin; and (c). The output signal is generally representative of a concentration of either one of the reactants or the products, though the signal that comes directly from the Raman probe will be converted to a concentration value as described herein to provide the output signal.

The process may further comprise the step of adjusting the olefin polymerization process in response to the output signal provided by the Raman spectrometry equipment. The olefin polymerization process can be adjusted by adjusting the concentration within the reaction mixture of at least one chemical component with the reaction mixture. Alternatively, the olefin polymerization process can be adjusted by adjusting one or more polymerization conditions selected from the group consisting of polymerization temperature, polymerization pressure, withdrawal of the reaction mixture from the reactor, and circulation rate of the reaction mixture within the reactor. The Raman spectrometry equipment is operatively connected to a Raman fiber optic probe that is in contact with the reaction mixture or the polyolefin.

In some preferred embodiments, the monomer consists of ethylene. In other preferred embodiments, a comonomer is present in the reaction mixture so that it is contacted with the ethylene, and the comonomer is selected from the group consisting of 1-butene, 1-pentene, 4-methyl-1-pentene, and 1-hexene.

The monitoring may be done using Raman spectrometry equipment to analyze effluent, such as the effluent from a loop polymerization reactor.

As another aspect, a method for monitoring and controlling an olefin polymerization reaction is provided. The method comprises (a) contacting components of a reaction mixture in a polymerization reactor under polymerization conditions, where the components comprise a monomer, a diluent, and a catalyst system; (b) using Raman spectrometry equipment to obtain a Raman spectrum; (c) obtaining a concentration of at least one component based upon the Raman spectrum; (d) adjusting at least one polymerization condition in response to the concentration of the component. The method may also comprise obtaining a Raman spectrum of the reaction mixture, and determining the concentration of at least one component through the use of a calibration model. In preferred embodiments, the method further comprises, prior to step (a), the step of developing the calibration model using partial least squares analysis.

As yet another aspect, an apparatus for olefin polymerization is provided. The apparatus comprises polymerization equipment comprising a polymerization reactor for slurry polymerization of one or more olefins, wherein the slurry comprises solid polymer particles and a diluent; at least one inlet to the reactor for providing chemical components of the polymerization; at least one outlet from the reactor for removing product from the polymerization reactor; at least one Raman probe located in the polymerization equipment, where the Raman probe provides an output signal; Raman spectrometry equipment located outside the polymerization equipment and operatively connected to at least one Raman probe.

The olefin polymerization apparatus may further comprises a computer that receives a signal from Raman spectrometry equipment. The computer can be operatively connected to flow control equipment for adjusting a concentration of at least one of the chemical components or the product. Alternatively, the computer can be operatively connected to equipment for adjusting one or more of polymerization conditions selected from the group consisting of polymerization temperature, polymerization pressure, withdrawal of the reaction mixture from the reactor, and circulation rate of the reaction mixture within the reactor. The computer may comprise a calibration model for converting Raman spectra to at least one concentration of one or more of chemical components or of product.

The Raman probe may be a Raman fiber optic probe disposed in the outlet or in polymerization reactor. The Raman probe can be operatively connected to the Raman spectrometry equipment by fiber optic cable.

In the present processes, methods and apparatus, low resolution Raman spectrometry equipment may be used, such as, for example, Raman spectrometry equipment having a resolution of about 15 wavenumbers to about 30 wavenumbers.

DETAILED DESCRIPTION OF DRAWINGS AND PREFERRED EMBODIMENTS

Figure 1:
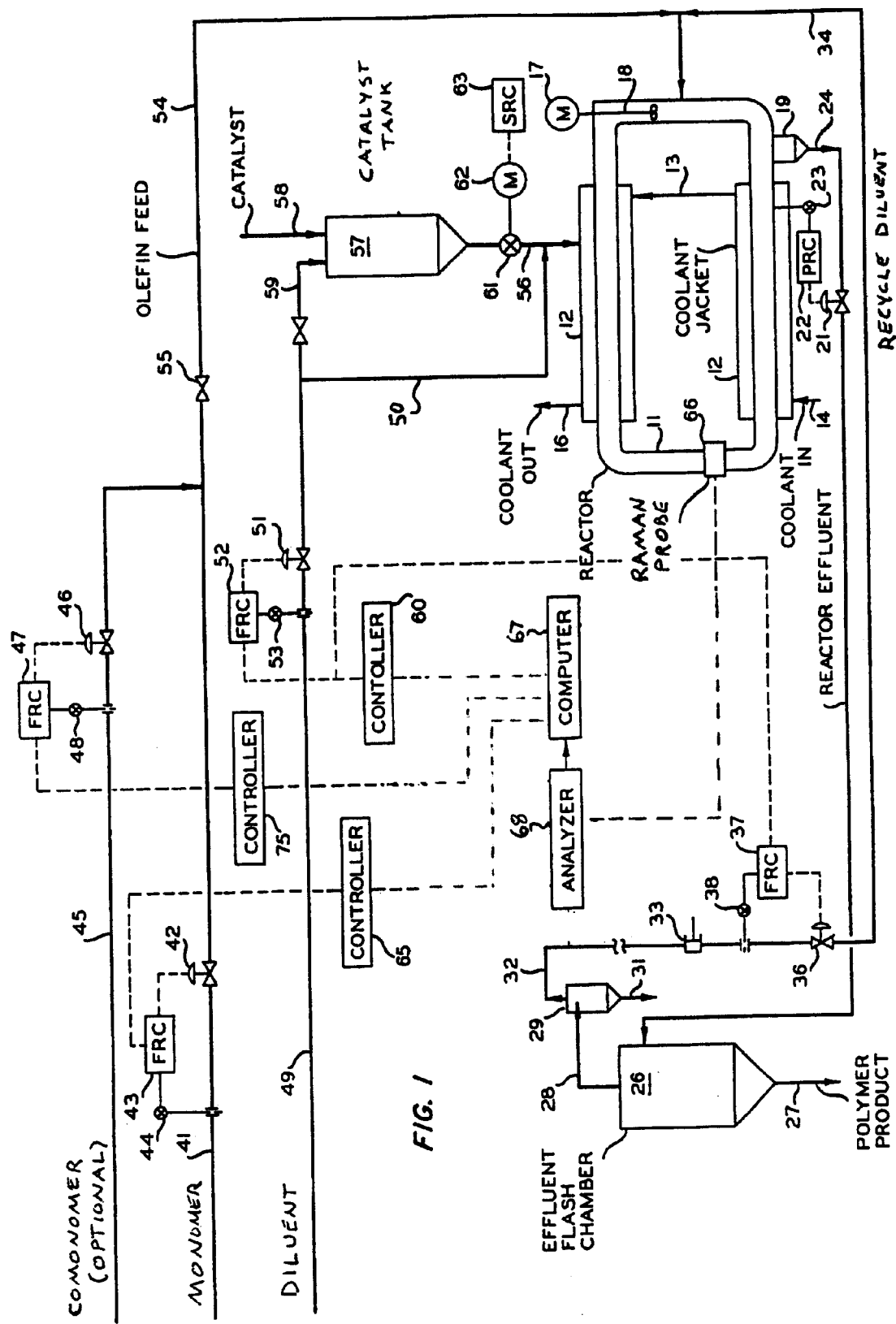
FIG. 1 is a diagram of a loop polymerization reactor comprising Raman spectrometry equipment for monitoring a slurry olefin polymerization process.

Some embodiments described herein are described in the terms of the polymerization of ethylene. However, the present processes and apparatus may be employed with any process where it is desired to monitor and control polymerization of an olefin. It is particularly applicable to the operation of loop reactors which produce polyethylene or polypropylene under slurry polymerization conditions. Polymerization conditions generally include the concentration of reactants, products and other chemical components, temperature, pressure, withdrawal rate from the reactor, and circulation rate within the reactor A process for polymerizing olefins is provided wherein monomer and/or comonomer and/or other components may be monitored before, during and/or after the polymerization reaction through Raman spectrometry. Such Raman spectrometry provides for improved monitoring and control of the process. In preferred embodiments, a Raman fiber optic probe is located in the reactor or in a product take-off line just outside the reactor and provides an output signal from which monomer and/or comonomer and/or diluent concentrations may be determined. The present processes, methods, and apparatus provide improved process control compared to process control based on flash gas analysis by gas chromatography.

Raman spectrometry typically comprises providing a source of electromagnetic radiation, transmitting radiation to a sample, collecting scattered radiation from the sample, separating or dispersing the energy of the scattered radiation, and detecting the radiation. Any suitable radiation source may be employed in the present method and apparatus, preferably a radiation source having a nominal wavelength of 785 nm, alternatively a radiation source having a nominal wavelength of 532 nm. Various Raman spectrometry equipment, as well as underlying principles, are disclosed in U.S. Pat. No. 5,652,653, which is incorporated herein by reference.

Suitable Raman analytical units include the low resolution Raman R-2000 and R-2001C, manufactured and marketed jointly by Ocean Optics, Inc. (Dunedin, Fla.) and Boston Advanced Technologies, Inc. (Marlboro, Mass.). Such low cost, low resolution Raman spectrometers have been found to be suitable for use in the present processes, methods and apparatus. The device consists of a solid-state diode laser with a thermoelectrically cooled charge-coupled device (CCD) array miniature detector in the R-2001C and a computer interface card. Various other and related apparatus for Raman spectrometry, as well as underlying principles, are disclosed in U.S. Pat. No. 5,652,653, which is incorporated herein by reference.

The laser in the R-2001C is a B&W diode laser set at 785 nm with a power of 500 mW. The fiber-optic probe has excitation and collection fibers that use filtering to remove most of the laser line signal from collection. The R-2001detector is a high-sensitivity 2048-element linear CCD-array configured to detect a range of signals from 200 to 2800 $cm^{-1}$ and has a grating density of 1200 lines per mm. The detector is thermoelectrically cooled to a constant temperature of 7° C. The cooling allows for a better signal, and the constant temperature prevents having to retake dark currents to avoid floating baselines, making it ideal for longer data collection periods. The R-2001 host software that comes with the spectrometer makes the data available to the user. Spectral resolution for such a spectrometer is about 15 $cm^{-1}$, which places it in the category of low resolution Raman spectrometry equipment.

Preferably, a Raman fiber optic probe is employed in the present processes, methods and apparatus. Suitable probes include the InPhotonics RP-785-01-05-SMA probe and the InPhotonics RP-785-100-01SMA probe. The InPhotonics probe is preferred for analysis where there are solids present such as in the slurry olefin polymerization reactor. It has been found that other Raman fiber optic probes are not presently operable in a slurry olefin polymerization reactor. Another supplier of Raman fiber optic probes is Kaiser Optical Systems, Inc., which is similar to the InPhotonics probe in good performance in rejecting back scattering radiation. In general, a suitable Raman fiber optic probe may be constructed by soldering metal coated, fused silica fiber optic cables into a protective metal sheath. This probe design provides a simple, reliable method of optically sampling and remotely monitoring a chemical composition in a harsh physical environment of a manufacturing process. It may be advisable to position optical filters near the sample to remove background-inducing radiation caused by the fused silica core of the fiber optic cable.

Fiber optic probes have been used to provide a means for transmitting radiation towards a sample and collecting the scattered radiation. Such probes may be constructed with combinations of fiber optics, lenses, and/or mirrors. In one construction, two or more fiber optic lines are secured closely together on the sample end. One or more of these fiber optic lines (typically, one) are used to transmit the radiation into the sample, and one or more additional fiber optic lines (typically, more than one) are used to collect and transmit the scattered radiation back to a detector.

Thus, the same Raman probe may emit radiation and then detect the Raman scattered radiation. Radiation such as laser light may come out one part (for example, one fiber cable) of the Raman probe and is focused into the sample to be measured. When the radiation contacts the molecules in the sample, it excites those molecules to a virtual state, which is a high vibration energy level. When that molecule relaxes and comes back to its ground state, it scatters radiation in all directions. Some of the scattered radiation returns to the Raman probe, where it is gathered by another part (for example, other fiber optic cables) of the Raman probe and fed to the detector. Some of the scattered radiation that returns to the Raman probe reflects the molecular vibrations of the different molecules in the sample. The molecule emits a photon at the vibrational energy at which the molecule is vibrating when it was contacted by the radiation. The various molecules and vibrational energies scatter radiation of different energy levels, which have wavelengths, thereby forming a spectrum.

After the scattered radiation has been collected and transmitted, it is separated using a dispersion element. The dispersion element, which is typically included along with focusing and collimating optical elements in a spectrograph, facilitates the separation of various energy levels of the scattered radiation from one another.

Raman spectrometry has previously been used as the basis for an on-line analytical method, as disclosed in U.S. Pat. No. 5,652,653. The present processes, methods, and apparatus differ from the disclosure of that patent at least in that the present processes and apparatus do not employ simultaneously irradiation of a reference material.

The present processes, methods and apparatus are particularly useful for in situ monitoring of an olefin polymerization process. In the present methods, both liquid phase and gas phase concentrations may be determined by Raman analysis, while this was not readily done by other techniques. Generally, separate Raman probes will be positioned in the gas phase and the liquid phase. The use of results of liquid phase and gas phase analyses may provide faster and more accurate results than from current gas chromatographic analyses of flash gas.

Alternatively, monitoring of the olefin polymerization process may be accomplished by conducting Raman spectrometry at several points or times before, during and/or after the polymerization process, thereby providing a method of monitoring the polymerization reaction as it proceeds. For example, one might measure the concentrations of monomer, comonomer, hydrogen, and/or other reactants or diluents as they go into a polymerization reactor, and/or into a diluent such as isobutane, and/or in the flash gas.

As another alternative, the present processes and methods may be used to control two or more reactors in series. For example, the effluent from effluent from an upstream reactor may be provided as input to a downstream reactor for additional polymerization of the effluent. However, it may be desirable to supply an additional amount of monomer and/or comonomer to the second or other later reactor (a reactor other than the first reactor in series), and that amount can only be determined by rapid analysis of the components of the input. When reactors are connected in series, a monitoring step may include determining a concentration of the monomer in the effluent of the upstream reactor by Raman spectrometry equipment, and an adjusting step may include providing an amount of monomer or comonomer in addition to the effluent to the downstream reactor.

By using the present process with reactors in series, one can get more desirable properties in the product, including polyolefins having a desired bimodal or multimodal molecular weight distribution and/or having a comonomer selectively incorporated into the polyolefin at the high end of the molecular weight distribution. Additionally, residual monomer in the effluent may be polymerized into product, thereby increasing the efficiency of the process.

Referring to FIG. 1, there is illustrated a loop polymerization reactor 11 and associated equipment for the polymerization process. This loop polymerization reactor provides a continuous path of circulation of the reaction slurry or reaction mixture. In this embodiment, the loop reactor 11 is jacketed by heat exchange sections 12 which are connected by line 13 and contain a heat exchange medium supplied by line 14 and removed by line 16 for maintaining the loop reactor 11 at a desirable temperature. The reactor 11 is provided with suitable agitation or circulating equipment, such as a propeller or stirrer 18 driven by a motor 17. In this type of reactor, the reaction mixture is circulated through the reactor at a velocity that provides highly turbulent flow, for example, about 21 feet/second. The reaction effluent from the reactor 11 is withdrawn through a product take-off line 19 and passed to a settling leg 24 which can be a drain or vertical leg. In preferred embodiments, the reaction effluent is a slurry made up of polyethylene, unreacted ethylene, unreacted comonomer, and isobutane, and the catalyst is generally contained in the polyethylene. A suitable apparatus for controlling the removal of polymerization reaction effluent is disclosed in U.S. Pat. No. 5,565,174, which is incorporated herein by reference. The withdrawal of effluent is regulated by suitable equipment, such as a flow rate control valve 21, pressure regulator controller 22, and pressure sensor and transmitter 23, such withdrawal equipment being dependent upon reactor pressure.

Withdrawal of the reaction mixture may be continuous or intermittent. In the case of continuous withdrawal, changes in volumetric reactor input causes changes in valve opening in the product conduit 19 to maintain constant reactor pressure. In the case of intermittent withdrawal, changes in volumetric reactor input causes changes in the time interval between valve openings to maintain constant reactor pressure. Some of the reactant, diluent, and catalyst are withdrawn along with product.

The reactor effluent is passed through line 24 to a suitable product separator, such as a flash tank 26. The pressure of the reactor effluent is lowered in the flash tanks. Preferably, two or more flash tanks are employed in series, because using more than one flash tank may provide better recovery of polyolefin. In flash tank(s) 26, the polyolefin product is separated from the reaction effluent and passed through line 27 to suitable finishing equipment, such as dryers. The vaporized components of the reaction mixture comprising unreacted reactants and diluent are withdrawn through line 28 from flash tank 26 and passed to a suitable cyclone chamber 29 to ensure removal of polyolefin fines, which are withdrawn through line 31. The polyolefin-free vapors are then passed by line 32 to other separation equipment (indicated by the break in line 32) to further separate reactant from diluent, which is compressed by compressor 33 and recycled back to the reaction system by line 34 with the olefin feed. Recycle line 34 can be provided with the usual flow control equipment, such as flow rate control valve 36, flow rate controller 37, and differential pressure transmitter 38.

In the embodiment shown in FIG. 1, a monomer such as ethylene or propylene is supplied from conduit 41, which may have flow control apparatus such as the flow rate control valve 42, flow rate controller 43, and differential pressure transmitter 44. A comonomer may be provided from conduit 45, and the flow rate of comonomer may be regulated by flow control apparatus such as flow rate control valve 46, flow rate controller 47, and differential pressure transmitter 48. A diluent, such as isobutane, pentane, isopentane, mixtures thereof, or other suitable paraffins having 3 to 12 and preferably 3 to 8 carbon atoms per molecule, is supplied through conduit 49, and its flow rate may be regulated by flow control apparatus such as flow rate control valve 51, flow rate controller 52, and differential pressure transmitter 53. The diluent may be provided to reactor 11 directly by line 50 and/or indirectly through the catalyst feed system described below. The monomer and comonomer feeds can be combined and passed by a common olefin feed stream 54 to reactor 11. The mixture of olefin reactants in line 54 is established at a substantially constant pressure, for example 600 psi, by a pressure control valve 55.

A catalyst system, such as chromium oxide on silica or a silica-titanium catalyst, is provided from conduit 58 and introduced to reactor 11 after mixing with some diluent from line 59 in catalyst tank 57. Any catalyst system suitable for polymerizing olefin may be employed with the present processes and apparatus. In slurry polymerization processes, it is particularly preferred to employ heterogeneous catalyst systems comprising one or more catalytic metal compounds, and co-catalysts such as an alkylaluminum or aluminoxane, perhaps with a support material such as silica. In FIG. 1, the catalyst flow rate is regulated by flow control apparatus such as a suitable rotary valve 61 driven by a motor 62, which is controlled by speed rate controller 63. The concentration of catalyst in the reaction mixture can vary widely, particularly depending on the type of catalyst used, however, it will generally comprise 0.001 to 5 percent by weight based on the liquid hydrocarbon diluent. The catalyst injection rate can be controlled by means of a heat balance computer or other means to maintain a constant rate of polymer production.

The reaction mixture circulates in the loop, where monomer contacts catalyst under suitable polymerizations conditions. As a result of contacting monomer (and comonomer, when present) with the catalyst under such conditions, a polymerization reaction takes place and a polyolefin is formed. The polyolefin generally forms as solid particles in the reaction mixture. The solid polyolefin particles in the liquid diluent form a slurry.

The polymerization reaction, or one or more its components or conditions, may be monitored. The monitoring equipment shown in FIG. 1 includes a Raman probe 66, which for clarity is shown as a box surrounding the loop reactor 11 but which is typically disposed mostly or entirely within the reactor 11. The Raman probe 66 provides an output signal which is representative of the Raman spectrum of the chemical components in reactor 11 or some portion of those components. The output signal from Raman probe 66 is provided to an analyzer 68 which in turn provides a signal to computer 67. Information transmittal paths and signal paths are shown in FIG. 1 by dashed lines. The physical form of those paths may vary. In computer 67, the Raman spectrum is monitored, and the polymerization process may be controlled manually or automatically in response to the spectrum. For example, computer 67 may send a signal (represented in FIG. 1 by dashed lines) to one or more of controllers 60, 65, 75 to adjust the amounts of reactants or diluent added to the loop reactor or the amount of material withdrawn. Alternatively, computer 67 may send a signal to one or more of motor 17 (to adjust the circulation of reaction mixture), pressure regulator controller 22 (to control the withdrawal of product), or valve 61 (to control the amount of catalyst provided to reactor 11).

The Raman spectrum may be used to determine the concentrations of the chemical components in the reactor, and/or before or after the reactor. The Raman spectrum may be used to determine the concentration of polyolefins such as polyethylene and polypropylene, reactants such as ethylene monomer and hydrogen, and diluents such as isobutane.

The peaks of the Raman spectra, or some number that represents such peaks, should be correlated to known concentrations of components through a calibration model before Raman spectrometry is used to determine unknown concentrations. One method of obtaining numerical representation of a peak of the Raman spectrum is by integrating the area of the peak to obtain a single number that represents that peak. One may use a wavelength that is characteristic of a certain component and integrate the area of the peaks at that wavelength to arrive at a number representative for that component. The peaks, or area of the peaks, or some other number representative of certain parts of the Raman spectrum, must then be correlated to a known concentration using a calibration model, which may be based on assigning an area under a certain peak to a known concentration.

In a general procedure for developing a suitable calibration model, a Raman spectrum is obtained for a sample of known concentration of one component, or more preferably a mixture of components, that will be the subject of analysis in the olefin polymerization process. A plurality of separate regions of the spectrum are selected, based on the known Raman spectra of the components. For example, there is a peak at 16 to 20 wavenumbers that is characteristic of ethylene, so where ethylene will be one of the chemical components of interest, the region of the spectrum at 1620 wavenumbers would likely be selected. Next, the areas of the selected regions are determined. A correlation is then identified between the area of the selected region and the concentration of the component(s). By repeating this procedure for different concentrations and different components, and preferably by obtaining multiple spectra and making multiple calculations for each concentration and component, a calibration model may be obtained for the chemical components to be analyzed and monitored. A procedure for the development of a means within a computer for identifying substances using Raman spectroscopy is disclosed in U.S. Pat. No. 4,620,284.

Certain peaks may be known to correspond to a particular component, such as either the polyolefin product or the monomer. However, other peaks may correspond to more than one component or may be indistinguishable from each other although they correspond to different components. In such cases, obtaining a calibration model that can distinguish and correct quantify these components may seem impossible. It has been observed that such a calibration model is obtainable, though with more difficulty than where the components have peaks that are separate and readily distinguishable. Furthermore, it has been discovered that such a calibration model may be obtained and used even with low resolution Raman spectrometry equipment.

A calibration model is developed by measuring a sample using the Raman spectrometry equipment, and obtaining a Raman spectrum. The spectrum, or the integrated area or intensity of the peaks of that spectrum, are related to some value, preferably the concentration of monomer or other chemical component as measured by a gas chromatograph. For example, a Hewlett Packard 6890 with a flame ionization detector may be employed, with a capillary column that is a 60 meter DB1, 0.32 ID, column with a 1 micrometer film thickness. The gas chromatograph may be programmed to start at 40° C., hold for ten minutes, and then increase temperature 12° C. per minute until it reached 275° C. The analysis time for each sample should be approximately forty to forty-five minutes.

The concentrations determined by another analysis or by using a specially made sample having a known concentration are correlated to the Raman spectrum or parts of the spectrum and used to develop a calibration model. The calibration model can then be used to determine or predict unknowns. A calibration model may be created using commercially available software, such as the GRAMS/32 and PLSplus/IQ programs available from Galactic Industries Corporation (Salem, N.H.). The calibration model may be calculated and future unknowns may be predicted using the Galactic GRAMS/32 program. One may employ additional statistic or computational analysis to confirm or refine the correlation between chemical concentrations and the peaks generated by Raman spectrometry analysis. For example, one may perform partial least squares regression analysis, using the Galactic PLSplus/IQ program. Partial least squares analysis enables the development of a calibration model where one or more components may have some peaks that overlap. A calibration model may predict the concentrations based on what is known and assign concentrations to the unknowns.

Generally, suitable software must be capable of building models between spectral data and concentrations or other characteristics determined some other method and which have a relationship to the spectral response. Such software is typical and commercially available.

In an example of the development of a calibration model, a Raman Systems R-2001C spectrometer was placed in a polyethylene pilot plant control room, and an InPhotonics RP-785-100-01-SMA probe was placed about 100 feet away in the settling leg product take-off line of a polyethylene reactor. A process gas chromatograph measured the concentrations of ethylene, hexene and isobutane in the reactor flash gas. The spectra from the Raman Systems R-2001C unit and the GC analyzer data were entered into the Grams/32 PLS-1 model to build the calibration model.

The Grams/32 PLS-1 calibration file had the following parameters: Calibration Type: PLS-1, Diagnostic: Cross Validation, # Regions: 1 (1750–0 cm$^{-1}$), # Samples: 34, # Points: 1280, Maximum # Factors: 16, # Files Out: 1, Preprocessing: Mean Centering with Auto Baseline. No samples were excluded and no constituents were excluded. The recommended number of factors was 5. The actual versus predicted values for ethylene had an $R^2=0.925$ for the range 0 to 12 mol %. The actual versus predicted values for hexene had an $R^2=0.978$ for the range 0 to 5.5 mol %. The actual versus predicted values for isobutane had an $R^2=0.929$ for the range 80 to 96 mol %.

By use of this model, we were able to predict ethylene and hexene concentrations within 11% of the GC analyzer value, which is an acceptable error range. With this level of accuracy, it is possible to effectively monitor the concentration of ethylene and hexene in the liquid phase of the reactor.

Additionally, the present processes and apparatus may be automated through the use of the computer 67, microprocessor, programmably logic controller or other suitable device to automatically adjust one or more conditions in response to the output signal from the Raman probe and/or the Raman analyzer.

Vibrations, movements, and shifting of the various Raman spectrometry equipment can cause unexpected changes in the observed spectra. The types of errors induced are difficult to predict and may cause inaccuracies that result in limited precision. It is desirable to eliminate or minimize the effects of vibrations, movements, and shifting in the Raman spectrometry equipment.

Sample probes may be placed at any location before, during and/or after the olefin polymerization process, but it is generally advisable to place the Raman probe where it will provide information that is useful for controlling the process and for providing analytical information for calibration purposes. One preferable Raman probe location in a polyolefin production process is near the point in the process where the polymerization reaction is near completion. This provides analytical information regarding extent of reaction. Such information allows for improved control of the polymerization process.

In the present methods and apparatus, there are two aspects with respect to the placement of the Raman probe. In one aspect, the Raman probe is placed in the reactor such that it analyzes the slurry having a concentration of solid polymer in a liquid containing diluent and reactants. The slurry may typically comprise 50 weight percent solids. The Raman probe is exposed to and measures polymer, diluent and reactants. It has been observed that the polyolefin particles tend to diffract or scatter the emitted light such that it is not observed by the Raman probe. As a result, the presence of polyolefin particles may lower the signal intensity to about one-tenth of what it would be in a clear liquid. One problem with Raman spectrometry in a slurry is that a substantial amount of scattered light does not come back to the detector. One response to this problem has been to place the Raman probe in the product removal area of the slurry loop polymerization process.

As another aspect, the Raman probe may be placed in a product take-off line, where the polymer settles out from the slurry, thereby forming a clear liquid, and the probe is pointing into the clear liquid. The clear liquid may contain diluent such as isobutane and reactants such as ethylene and hexene. These separate from the solid polymer after the slurry leaves the reactor in the product take-off line or in the settling leg. The polymer settles to the bottom and the clear liquid is above the polymer. In the polymerization reactor, a valve opens so that reaction slurry flows from the reactor into the product take-off line. After a suitable amount of polymer reaction slurry flows into the product take-off line, the valve closes and there is a certain dwell time, such as about 30 seconds, during which the polyolefin is allowed to settle by gravity to the bottom of the settling leg. The Raman probe may be pointed in the top, which is the clear liquid. For a relatively short time, perhaps about three seconds, the Raman probe is exposed to the slurry, but for a longer time, perhaps about 27 seconds, the probe is only exposed to the clear liquid because polyolefin settles out rapidly. It is advantageous to minimize the loss of scattered radiation caused by the solid polyolefin particles.

It has been found that monitoring in the settling leg using Raman spectrometry is better and quicker than monitoring at the flash tanks using gas chromatography. The flash chamber is downstream from the settling leg, and in the dual-stage flash system frequently used with loop reactors operating at pressures of about 600 psi, the reaction mixture is dropped from about 600 psi to about 300 psi in the first flash chamber and then down to 15 psi in the second flash chamber. The gas chromatograph in the first flash chamber takes about six minutes for its analysis and the gas chromatograph in the low pressure flash chamber takes about six minutes for its analysis. One must add those two times together, and so it takes 12 to about 15 minutes to complete the entire gas chromatographic analysis of the flash gas. Further, it is disadvantageous to employ two numbers which are obtained at two different pressures (for example, 300 psi and 15 psi) and it may lead to some errors in the gas chromatographic method. In contrast, Raman analysis of the clear liquid in the product take-off line is a few seconds away from the reactor, and an analysis may be obtained more quickly.

An alternative process is the conversion of ethylene to 1-hexene. The reaction mixture in this process is itself a homogenous clear liquid, so the Raman probe may be used in the reactor without the negative effects observed from solid polyolefin particles. In the 1-hexene process, as well as other processes involving clear liquids, the Raman probe may be optimally placed in the reactor or in a sampling line.

Furthermore, it may be advantageous to develop a calibration model for Raman spectrometry equipment to be used in a slurry olefin polymerization process by calibrating in a 1-hexene process. For example, the Raman probe may be placed in the sampling line for the gas chromatograph system of a 1-hexene process. Then, data from the Raman system and the gas chromatograph system are obtained for the same liquid. Those data may be used to correlate the Raman spectra to concentrations determined by the gas chromatograph and develop a calibration model.

However, in a slurry polymerization process, the Raman probe may also be placed in the reactor where it is in contact with the slurry. It has been observed that there may be about a ten-fold reduction in signal, but some of the newer probes, such as from InPhotonics, are capable of detecting the lower levels of scattered light from the slurry.

The ability to use low resolution Raman spectrometry systems is surprising, in that such systems are typically not capable of resolving ethylene peaks from hexene peaks. However, the way the band shapes change, base line solution is not required, and modeling software can be used to detect concentrations without resolving individual peaks. In other words, it is not necessary to resolve the peaks corresponding to ethylene and hexene in the present methods. This is similar to what is done in near-infrared spectrometry, so that one uses partial least square techniques to analyze those. The ability to use a low resolution Raman spectrometer makes the present methods more economical. High cost, high resolution Raman spectrometry equipment generally have a resolution of one to two wavenumbers and can resolve peaks that are only one or two wavenumbers apart. However, it has been discovered that such high resolution is not required for the present processes. A low resolution Raman spectrometer having lower cost may be used. Its resolution may be from about 15 wavenumbers to about 30 wavenumbers. As a result, the low resolution Raman spectrometry equipment cannot resolve as many peaks as the high resolution spectrometer, but it has been discovered that it is not necessary to have one to two wavenumber resolution for monitoring concentration of components in an olefin polymerization process. In the preferred embodiments, the detector element is capable of discerning extremely low levels of radiation.

While the invention has been described in connection with one or more embodiments, it will be understood that the invention is not limited to those embodiments. On the contrary, the invention includes all alternatives, modifications, and equivalents as may be included within the scope of the claims.

What is claimed is:

1. A process for olefin polymerization in a slurry comprising solid polyolefin and a diluent, said process comprising the steps of:
   (a) contacting in a reaction mixture under slurry polymerization conditions:
      (i) at least one reactant comprising at least one olefin monomer and optionally at least one comonomer and optionally hydrogen;
      (ii) a heterogeneous catalyst system comprising one or more catalytic metal compounds and one or more co-catalysts;
   (b) making a polyolefin; and
   (c) monitoring the process by using Raman spectrometry equipment to provide an output signal representative of one or more of said reactants or said polyolefin; and
   (d) adjusting the olefin polymerization process in response to the output signal provided by the Raman spectrometry equipment by adjusting one or more polymerization conditions selected from the group consisting of polymerization temperature, polymerization pressure, withdrawal of said reaction mixture from said reactor, and circulation rate of said mixture within said reactor.

2. The olefin polymerization process of claim 1, wherein said output signal is representative of a concentration of one of said reactants or said polyolefin.

3. The olefin polymerization process of claim 1, wherein the olefin polymerization process is adjusted by adjusting the concentration within said reaction mixture of at least one chemical component.

4. The olefin polymerization process of claim 1, wherein said Raman spectrometry equipment is operatively connected to a Raman fiber optic probe that is in contact with said reaction mixture or said polyolefin.

5. The olefin polymerization process of claim 4, wherein said Raman fiber optic probe comprises a metal coated, fused silica fiber optic cable contained within a protective metal sheath.

6. The polymerization process of claim 1 wherein said Raman spectrometry equipment comprises low resolution Raman equipment.

7. The polymerization process of claim 6 wherein said Raman low resolution spectrometry equipment has a resolution in the range of from about 15 wavenumbers to about 30 wavenumbers.

8. The method of claim 1, wherein said at least one monomer consists of ethylene.

9. The method of claim 8, wherein a comonomer is contacted with said ethylene, and said comonomer is selected from the group consisting of 1-butene, 1-pentene, 4-methyl-1pentene, and 1-hexene.

10. A process for olefin polymerization in a slurry comprising solid polyolefin and a diluent, said process comprising the steps of:
    (a) contacting in a reaction mixture under slurry polymerization conditions within a loop polymerization reactor:
       (i) at least one reactant comprising at least one olefin monomer and optionally at least one comonomer and optionally hydrogen;
       (ii) a heterogeneous catalyst system comprising one or more catalytic metal compounds and one or more cocatalysts;
    (b) making a polyolefin; and
    (c) monitoring the process by using Raman spectrometry equipment by analyzing effluent from said loop polymerization reactor to provide an output signal representative of one or more of said reactants or said polyolefin.

11. A process for olefin polymerization in a slurry comprising solid polyolefin and a diluent, the process comprising the steps of:
    (a) contacting in a reaction mixture under slurry polymerization conditions:
       (i) at least one reactant comprising at least one olefin monomer and optionally at least one comonomer and optionally hydrogen;
       (ii) a heterogeneous catalyst system comprising one or more catalytic metal compounds and one or more cocatalysts;
    (b) making a polyolefin;
    (c) monitoring the process by using Raman spectrometry equipment to provide an output signal representative of one or more of said reactants or the polyolefin; and
    (d) adjusting the olefin polymerization process in response to the output signal provided by the Raman spectrometry equipment;
       wherein the olefin polymerization process is performed in two or more reactors connected in series, wherein effluent from an upstream reactor is provided as input to a downstream reactor, wherein the monitoring step comprises determining a concentration of the monomer in the effluent by Raman spectrometry equipment, and the adjusting step comprises providing an amount of monomer or comonomer in addition to the effluent to the downstream reactor.

12. A method for monitoring and controlling an olefin polymerization reaction comprising:
    (a) contacting components of a reaction mixture in a polymerization reactor under polymerization conditions, said components comprising a monomer, a diluent, and a catalyst system;

(b) using Raman spectrometry equipment to obtain a Raman spectrum;

(c) obtaining a concentration of at least one said component based upon said Raman spectrum;

(d) adjusting at least one polymerization condition in response to said concentration of said component.

13. The method of claim 12, said measuring comprises: obtaining a Raman spectrum of said reaction mixture, and determining said concentration of at least one of said components through the use of a calibration model.

14. The method of claim 13, further comprising, prior to step (a), the step of developing said calibration model using partial least squares analysis.

15. The method of claim 14, wherein said Raman spectrometry equipment is low resolution Raman spectrometry equipment.

16. The method of claim 15, wherein said low resolution Raman spectrometry equipment has a resolution of about 15 wavenumbers to about 30 wavenumbers.

17. The method of claim 13, further comprising, prior to step (a), the step of developing the calibration model for said Raman spectrometry equipment to be used in the olefin polymerization reaction by calibrating in a process for converting ethylene to 1-hexene.

* * * * *